US005346820A

United States Patent [19]

Antranikian et al.

[11] Patent Number: 5,346,820

[45] Date of Patent: Sep. 13, 1994

[54] **THERMOSTABLE PROTEASE FROM *THERMOBACTEROIDES***

[75] Inventors: Garabed Antranikian, Seevetal 1-Hittfeld; Michael Klingeberg, Gronau, both of Fed. Rep. of Germany

[73] Assignee: Novo Nordisk A/S, Bagsvaerd, Denmark

[21] Appl. No.: 938,268

[22] Filed: Oct. 22, 1992

[30] Foreign Application Priority Data

Jun. 15, 1990 [DK] Denmark ............................ 1459/90

[51] Int. Cl.[5] ........................ C12N 9/48; C12N 9/50; C12N 9/52; C11D 10/00

[52] U.S. Cl. .................................. 435/220; 435/212; 435/219; 252/174.12

[58] Field of Search ...................... 435/212, 219, 220; 252/174.12

[56] References Cited

U.S. PATENT DOCUMENTS 3,796,635 3/1974 Delente ................................ 195/65
4,480,036 10/1984 Morgan et al. .................... 435/220

FOREIGN PATENT DOCUMENTS

WO90/10072 9/1990 PCT Int'l Appl. .

OTHER PUBLICATIONS

Ollivier et al, (1985) *Int. J. Syst. Bacteriol.,* 35(4), 425–428.
Toda et al. (1988) *Agric. Biol. Chem.,* 52(6), 1339–1344.
Cowan et al. (1987) *Biochem. J.,* 247, 121–133.
Kelly et al. (1988) *Biotechnol. Prog.,* 4(2), 47–62.
Cowan et al. (1985) *Trends Biotechnol.,* 3(3), 68–71.
Bragger et al. (1989) *Appl. Microbiol. Biotechnol.,* 31(5/6), 556–561.
Cowan et al, (1982) *Biochim. Biophys. Acta.,* 705, 293–305.
Stetter et al, (1986) *Experientia,* 42(11/12), 1187–1191.
Fusek et al. (1990) *J. Biol. Chem.,* 265(3), 1496–1501.
Daniel (1992) *Origin Life Evol. Biosph.,* 22, 33–42.
Eggen et al. (1990) *FEMS Microbiol. Lett.,* 71(1/2), 17–20.
Blumentals et al. (1990) *Appl. Environ. Microbiol.,* 56(7), 1992–1998.
Borman (Nov. 4, 1991) *Chem. Eng. News.,* 31–34.
Cowan et al., Chem. Abstract, vol. 108, No. 5, p. 278, Abs. No. 33917f (1987).
Zamost et al., Chem. Abstract, vol. 114, No. 13, p. 308, Abs. No. 117332y (1990).
Takii et al., Chem. Abstract, vol. 108, No. 15, p. 332, Abs. No. 127292a (1987).
Horikoshi et al., Chem. Abstracts, vol. 82, No. 1, p. 244, Abs. No. 2625z (1974).
Inoue et al., Chem. Abstracts, vol. 112, No. 1, p. 618, Abs. No. 6098r (1989).
Miki Kubo, Patent Abstracts of Japan, vol. 12, No. 472, C551, Abstract of 63-192387 (1989).

*Primary Examiner*—David M. Naff
*Assistant Examiner*—Jon P. Weber
*Attorney, Agent, or Firm*—Steve T. Zelson; Elias J. Lambiris

[57] ABSTRACT

This invention is within the field of thermostable proteases. More specifically, the present invention relates to a thermostable protease from Thermobacteroides proteolyticus, to a process for the preparation of these enzymes, and to detergent compositions comprising these enzymes. The enzyme has a temperature optimum in the range of from 75 to 95° and a pH optimum in the range of from 6.5–10.0.

13 Claims, 1 Drawing Sheet

Activity (%)
Activity (%)
0 20 40 60 80 100
40 50 60 70 80 90 100
Temperature (°C)

THERMOSTABLE PROTEASE FROM *THERMOBACTEROIDES*

TECHNICAL FIELD

This invention is within the field of thermostable proteases. More specifically, the present invention relates to novel thermostable proteases, to a process for the preparation of these enzymes, and to detergent compsitions comprising these enzymes.

BACKGROUND ART

It is known from International Journal of Systematic Bacteriology, Oct. 1985, p. 425–428, Vol. 35, No. 4 that a strain of *Thermobacteroides proteolyticus* ferments peptone, gelatin and casein. Protease from *Thermobacteroides* has never been isolated or characterized, nor has any use for such a protease been suggested.

BRIEF DISCLOSURE OF THE INVENTION

Within the scope of the present invention novel enzymes that show extraordinary thermostability as well as thermoactivity are provided. Accordingly, in its first aspect, the present invention provides a protease that is characterized by having pH optimum in the range of from pH 6.5 to 10.0, and temperature optimum in the range of from 75 to 95° C. In another aspect, the present invention provides a protease that is characterized by having pH optimum in the range of from pH 6.5 to 10.0, temperature optimum in the range of from 75 to 95° C., and immunochemical properties identical or partially identical to those of the protease derived from *Thermobacteroides proteolyticus,* DSM No. 5265.

In a third aspect, the present invention provides a process for the preparation of the thermostable proteases of the invention, which process comprises cultivation of a protease producing strain of Thermobacteroides in a suitable nutrient medium, containing carbon and nitrogen sources and inorganic salts, followed by recovery of the desired enzyme. In a preferred embodiment of this process, a strain of *Thermobacteroides proteolyticus* is cultivated. In a further preferred embodiment, *Thermobacteroides proteolyticus,* DSM No. 5265, or a mutant or a variant thereof, is cultivated.

BRIEF DESCRIPTION OF THE DRAWING

The present invention is further illustrated by reference to the accompanying drawing, in which.

DETAILED DISCLOSURE OF THE INVENTION

Figure 1B:
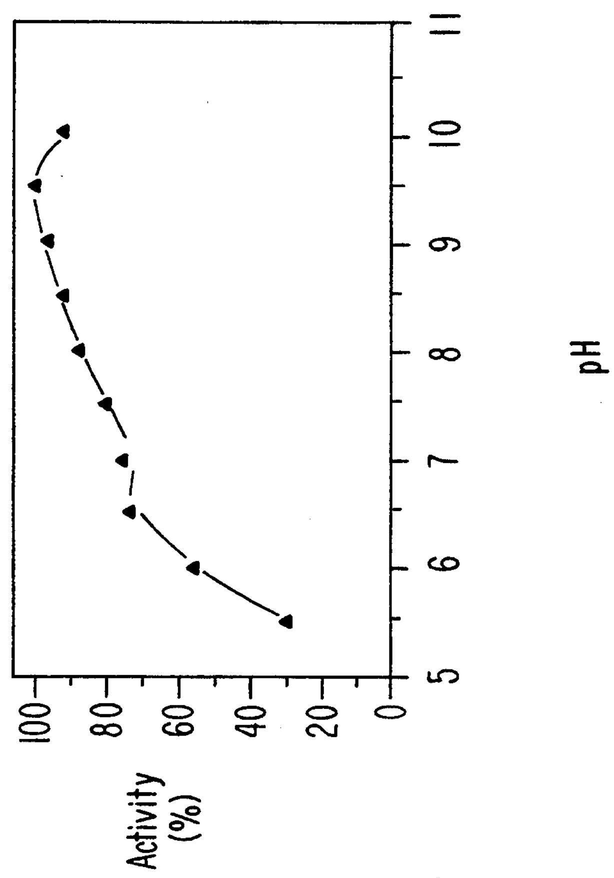
FIGS. 1A and 1B show the relation between the proteolytic activity of the protease obtained from *Thermobacteroides proteolyticus,* and temperature and pH, respectively.
Figure 1A:
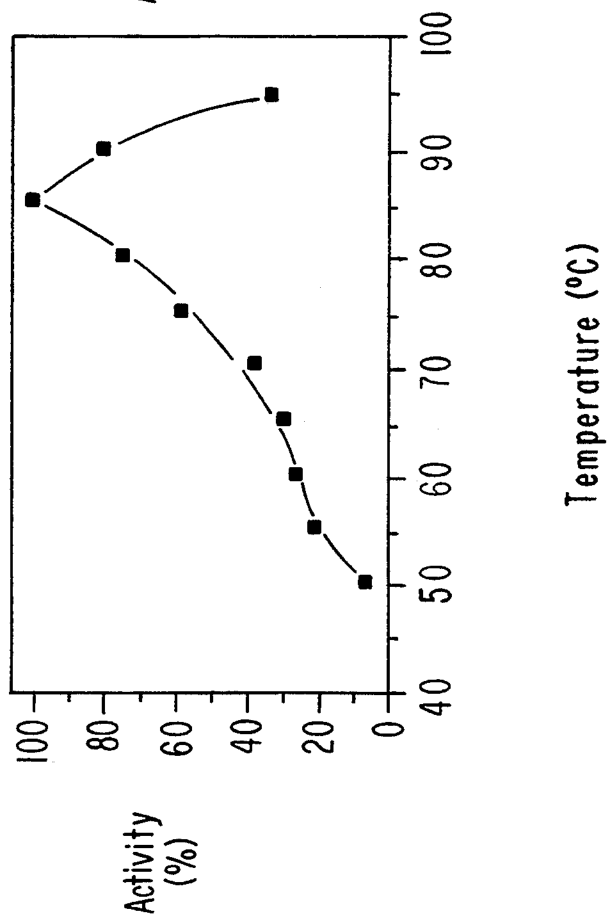

Growth experiments with Thermobacteroides have now shown that these organisms secrete extremely thermostable and thermoactive protein hydrolyzing enzymes. These enzymes possess proteolytic activity under extreme conditions. The properties of the Thermobacteroides proteases are demonstrated by the protease obtained from *Thermobacteroides proteolyticus.* A strain of *Thermobacteroides proteolyticus* is available from DSM, No. 5265.

As appears from the Figure, the protease obtainable from *Thermobacteroides proteolyticus* is active in a broad temperature and pH range, namely at temperatures of from below 50° C. to above 95° C., and at pH of from below 5.5 to above 10. The temperature optimum is between 75 and 95° C., more specifically between 80 and 90° C., around 85° C. Approximately 40% of proteolytic activity is still detected at 95° C. Moreover, it appears from the Figure that the relation between protease activity and pH leads to a flat activity curve, which means that the protease is very pH tolerant, possessing a generally high proteolytic activity over a broad pH range. In this way the proteases according to the invention have pH optimum in the range of from pH 6.5 to 10, more specifically between pH 8 and pH 10, yet more specifically between pH 9 and pH 10, around pH 9.5.

In table 1 some of the properties of the proteases obtainable from Thermobacteroides sp. are shown.

TABLE 1

| | *Thermobacteroides proteolyticus* |
|---|---|
| pH optimum | 9.0 |
| temperature optimum | 85° C. |
| type | serine |
| substrate specificity: | |
| Z-DL-Arg-pNA | − |
| Suc—Ala—Ala—Pro—Phe-pNA | + |
| Z-DL-Lys-pNA | − |
| Z-Gly—Pro-pNA | − |
| D-Phe—Pip—Arg-pNA | − |
| D-Val-L-Leu—Lys-pNA | + |

Suc = succinyl
pNA = p-nitroanilide
Pip = piperazine

Immunochemical properties

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenie identity" are described in the same book, chapters 5, 19 and 20.

Preparation of the proteases

The proteases according to the present invention are obtainable from members of the genus Thermobacterioides, e.g. *Thermobacterioides proteolyticus.*

The proteases of the invention can be prepared by cultivation of a protease producing strain of members of Thermobacteroides in a suitable nutrient medium, containing carbon and nitrogen sources and inorganic salts, and thus harvesting the desired enzyme.

The protease according to the present invention can also be prepared by recombinant DNA-technology.

Detergent compositions

Due to the unique properties of the proteases according to the present invention, these enzymes are of great interest for industrial applications, e.g. for use in the detergent industry.

The detergent composition of the invention may comprise one or more surfactants, which may be of an anionic, non-ionic, cat-ionic, amphoteric or zwitterionic type, or a mixture of these. Typical examples of anionic surfactants are linear alkyl benzene sulfonates (LAS); alkyl sulfates (AS); alpha olefin sulfonates (AOS); alcohol ethoxy sulfates (AES) and alkali metal salts of natural fatty acids. Examples of nonionic surfactants are alkyl polyethylene glycol ethers; nonylphenol polyethylene glycol ethers; fatty acids esters of sucrose and glucose; and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe. J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes, e.g. lipases; amylases; cellulases; and/or peroxidases, conventionally included in detergent compositions.

The protease of the invention may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates, liquids, in particular stabilized liquids, slurries, or protected enzymes. Dust free granulates may be produced according to e.g. GB 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol; a sugar or sugar alcohol; lactic acid or boric acid, according to established methods. Other enzyme stabilizers are well known in the art. Protected enzymes may be prepared according to the method disclosed in EP 238,216.

The following examples further illustrate the present invention.

EXAMPLE 1

Cultivation of *Thermobacteroides proteolyticus*

*Thermobacteroides proteolyticus,* DSM No. 5265, was cultivated in a nutrient medium containing the following components (per liter):

| Component | Amount |
|---|---|
| $KH_2PO4$ | 0.4 g |
| $NH_4Cl$ | 1.0 g |
| $MgCl_2.6H_2O$ | 1.0 g |
| $CaCl_2.2H_2O$ | 0.4 g |
| Yeast extract | 2.0 g |
| Trypticase BBL | 2.0 g |
| Trace element solution (see DSM-medium 141) | 10 ml |
| Resazurin | 1.0 mg |
| $NaHCO_3$ | 2.0 g |
| $Na_2S.9H_2O$ | 0.5 g |
| ad 1000 ml $H_2O$ dest. pH | 7.0–7.5 |

Cells were cultivated at 65° C. in a $N_2/CO_2$ (80/20) atmosphere.

The medium without sodium sulphide was boiled for 20 minutes, cooled on ice and dispensed under $N_2/CO_2$ (80/20) atmosphere. The medium was then filled under $N_2/CO_2$ (80/20) atmosphere into 100-ml vials. The medium was autoclaved at 120° C. for 20 min.

Before inoculation the medium was reduced by adding 10 ml/1 of sterile neutral sodium sulphide (3% solution). The medium was inoculated with 10% of a grown preculture and finally incubated at 65° C. for 36–48 hours.

Assay for proteolytic activity

The assay mixture contained 0.25% casein (Hammarsten) which was dissolved in 50 mM Tris/Glycine buffer, pH 9.0. The reaction was initiated by the addition of 250 μl enzyme sample to 2250 μl assay mixture at 85° C. Samples (500 μl each) were taken after 30, 60, 90 and 120 min. The reaction was stopped by cooling the samples on ice and by the addition of 500 ml of trichloroacetic acid (10% solution). The mixture was allowed to stand at room temperature for about 30 minutes and centrifugated afterwards for 10 minutes at 12,000 r.p.m. The absorbance of the supernatant was determined at 280 nm against a blank. 1 U of enzyme is defined as that amount of enzyme which liberates 1 μmol of tyrosine per minute under the specified conditions.

Characterization of the protease

Casein (Hammersten) was dissolved at a concentration of 0.25% in a buffer mixture which was composed of 20 mM MES (2-[N-Morpholino]ethanesulfonic acid), 20 mM HEPES (N-2-hydroxyethylpiperazine-N'-2-ethanesulfonic acid) and 20 mM Glycine at pH-values from 5.5 to 10, and at temperatures from 50 to 95° C.

As shown in the Figure, the level of protease activity reached a maximum around pH 9.5. At a pH value of 5.5 approximately 40%, and at a pH value of 10 approximately 90% of proteolytical activity could be detected. Optimum proteolytic activity for the substrate casein occurred at 85° C. Approximately 40% of enzyme activity was measured at 95° C., and approximately 10% of enzyme activity was measured at 50° C.

We claim:

1. An isolated protease which:

(a) has a pH optimum in the range of 6.5 to 10.0;

(b) has a temperature optimum in the range of 75 to 95° C.; and (c) is obtained from a strain of *Thermobacteroides proteolyticus.*

2. The isolated protease according to claim 1 which is obtained from the strain *Thermobacteroides proteolyticus,* DSM No. 5265.

3. An isolated protease according to claim 1 which has a pH optimum in the range of 8.0 to 10.0.

4. An isolated protease according to claim 1 which has a pH optimum in the range of 9.0 to 10.0.

5. An isolated protease according to claim 1 which has a pH optimum of around 9.5.

6. An isolated protease according to claim 1 which has a temperature optimum in the range of 80 to 95° C.

7. An isolated protease according to claim 1 which has a temperature optimum of around 85° C.

8. A process for producing a protease according to claim 1 comprising:

(a) cultivating a protease producing strain of *Thermobacteroides proteolyticus* in a suitable nutrient medium containing carbon and nitrogen sources and inorganics salts; and (b) recovering the protease.

9. The process according to claim 8, wherein the protease producing strain is *Thermobacteroides proteolyticus*, DSM No. 5265.

10. A detergent additive, comprising an isolated protease according to claim 1 in combination with a suitable excipient, wherein said detergent additive is in the form selected from the group consisting of a non-dusting granulate, a liquid, a slurry and a protected enzyme.

11. The detergent additive according to claim 10 which is in the form of a stabilized liquid.

12. A detergent composition comprising an isolated protease according to claim 1 and a surfactant.

13. The detergent composition according to claim 12, further comprising one or more other enzymes selected from the group consisting of amylase, lipase, cellulase and peroxidase.

* * * * *